Figure 1:
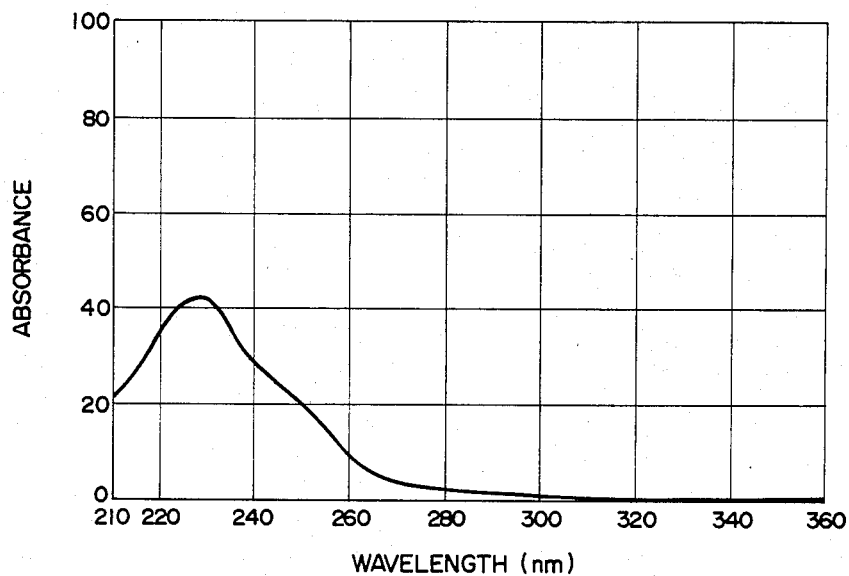

United States Patent [19]

Harada et al.

[11] Patent Number: 4,497,803

[45] Date of Patent: Feb. 5, 1985

[54] INCLUSION COMPOUND OF LANKACIDIN-GROUP ANTIBIOTIC AND USE THEREOF

[75] Inventors: Setsuo Harada, Kawanishi; Junya Okada, Hirakata, both of Japan

[73] Assignee: Takeda Chemical Industries, Ltd., Osaka, Japan

[21] Appl. No.: 482,553

[22] Filed: Apr. 6, 1983

[30] Foreign Application Priority Data

Apr. 12, 1982 [JP] Japan ................................. 57-61343

[51] Int. Cl.$^3$ .................. A61K 31/715; A61K 31/71; C07B 37/16
[52] U.S. Cl. .................................... 514/450; 514/546; 536/103; 536/7.1
[58] Field of Search ................ 424/180, 361; 536/103, 536/7.1

[56] References Cited

U.S. PATENT DOCUMENTS

| | | | |
|---|---|---|---|
| 2,959,580 | 11/1960 | Schlenk et al. | 536/1.1 |
| 3,869,443 | 3/1975 | Lesher et al. | 260/209 R |
| 4,073,931 | 2/1978 | Akito et al. | 424/298 |
| 4,228,160 | 10/1980 | Szejtle et al. | 424/180 |
| 4,407,795 | 10/1983 | Nicolau et al. | 424/180 |

OTHER PUBLICATIONS

Tsuchiya et al., *The Journal of Antibiotics*, vol. 24, pp. 29-41, (1971).
The Merck Index, p. 755, No. 5104.
The Merck Index, p. 893, No. 6100.
Kinashi et al., *Tetrahedron Letters*, vol. 22, No. 39, pp. 3861-3864.
S. Harada et al., The Journal of Antibiotics, 26, 647-657, (1973).
Central Patent Index; Basic Abstract Journal Section B: 21094 E/11, (Week E11, May 12, 1982).
W. Saenger, Angewandte Chemie International Edition in English, 19; 344-362, (1980).

*Primary Examiner*—Johnnie R. Brown
*Assistant Examiner*—Elli Peselev
*Attorney, Agent, or Firm*—Wenderoth, Lind & Ponack

[57] ABSTRACT

Inclusion compound of lankacidin-group antibiotic with cyclodextrin, having enhanced water-solubility and stability and a veterinary composition containing the same, which is useful for curing swine dysentery. The compound is prepared by adding lankacidin-group antibiotic to an aqueous cyclodextrin solution and stirring.

6 Claims, 6 Drawing Figures

INCLUSION COMPOUND OF LANKACIDIN-GROUP ANTIBIOTIC AND USE THEREOF

The present invention relates to inclusion compounds of lankacidin-group antibiotics. More particularly, it pertains to lankacidin-group antibiotic inclusion compounds with cyclodextrin and compositions containing the same.

The term "lankacidin-group antibiotic" is given to antibiotics having the formula (I) or (II);

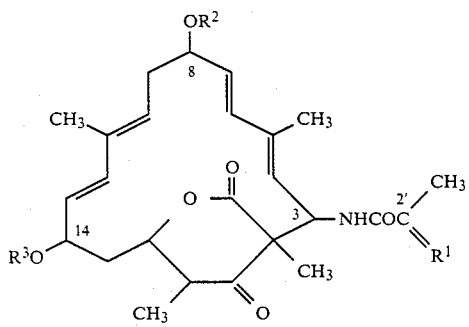

wherein $R^1$ is $=O$ or

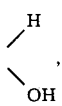

and $R^2$ and $R^3$ each represents hydrogen or lower alkanoyl,

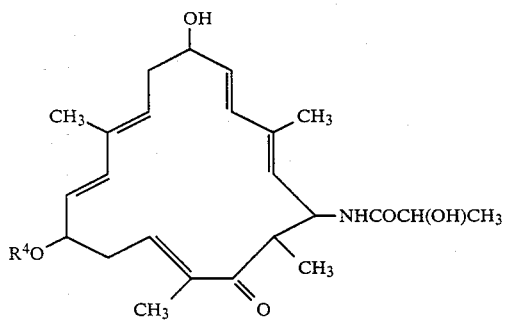

wherein $R^4$ is hydrogen or lower alkanoyl.

In the context of this invention, the term "lankacidin-group" means, generally, antibiotics having the above formulae (I) and (II) as a group, or a mixture of two or more of said antibiotics or, severally, any single species of the said antibiotics.

Lankacidin-group is also called antibiotic T-2636, and is produced by culturing microorganisms with or without further chemical or microbiological modifications. The microorganism to be cultured is, for example, *Streptomyces rochei* var. volubilis, which has been deposited at Fermentation Research Institute, Agency of Industrial Science and Technology, Tsukuba, Japan, Institute for Fermentation, Osaka, Japan, and The American Type Culture Collection, U.S.A., under the deposition Nos. FERMP-6155, IFO-12507, and ATCC-21250, since Sept. 11, 1981, Mar. 1, 1967 and May 13, 1968, respectively.

Preferred lower alkanoyl groups for symbols $R^2$, $R^3$ and $R^4$ above are those having one to six carbon atoms, in particular one to three carbon atoms. There are, for example, lankacidin A (I; $R^1$: O, $R^2$: H, $R^3$: $COCH_3$), lankacidin C (I; $R^1$: O, $R^2$: H, $R^3$: H), lankacidin C 8-acetate (I; $R^1$: O, $R^2$:$COCH_3$, $R^3$: H), lankacidin C 8-propionate (I; $R^1$: O, $R^2$: $COCH_2CH_3$, $R^3$: H), lankacidin C 14-propionate (I; $R^1$: O, $R^2$: H, $R^3$: $COCH_2CH_3$), lankacidin C 8,14-diacetate (I; $R^1$: O, $R^2$: $COCH_3$, $R^3$: $COCH_3$), lankacidinol A (I; $R^1$: H, OH, $R^2$: H, $R^3$: $COCH_3$), lankacidinol (I, $R^1$: H, OH, $R^2$: H, $R^3$: H), lankacyclinol (II; $R^4$: H), and lankacyclinol A (II, $R^4$: $COCH_3$). Processes for preparing these lankacidins and the chemical structure, the physicochemical properties and the biological activities thereof have been known [The Journal of Antibiotics, Vol. 24, 1, 13, 23, (1971); ibid, Vol. 26, 647 (1973); Chemical Pharmaceutical Bulletin, Vol. 22, 99 (1974), ibid, Vol. 23, 2201 (1975)].

It has also been revealed that the lankacidin-group antibiotics are effective as antibacterial agents or antitumor agents [The Journal of Antibiotics, Vol. 24, 29 (1971); Cancer Chemotherapy Report, Vol. 59, 919 (1975)], and are effective against swine dysentery (British Patent Publication No. 2088715) with lower acute toxicities.

However, the lankacidin-group has disadvantages in that administration as medicines is very limited due to low solubility in water and unstability in an aqueous solution.

The present inventors have found that the lankacidin-group selectively form inclusion compounds with cyclodextrin and that such inclusion compounds are highly soluble in water with very high stability.

The present invention provides inclusion compounds of lankacidin-group with cyclodextrin, and a practical process for producing and compositions containing the same.

Figure 2:
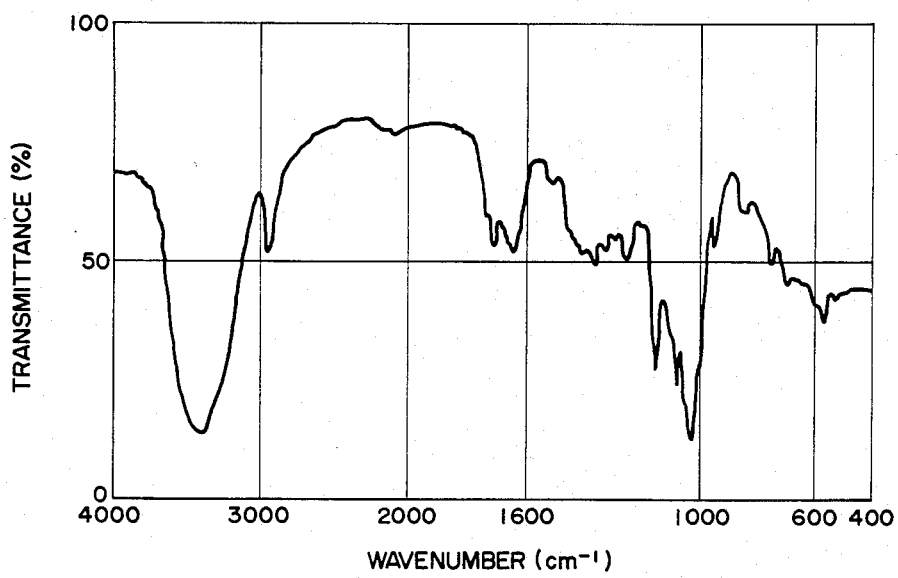

In the accompanying drawings, FIG. 1 and FIG. 2 are ultraviolet absorption spectrum (hereinafter referred to as "UV", in water), and infrared absorption spectrum (hereinafter referred to as "IR", KBr), respectively, of the present inclusion compound of lankacidin A prepared in Example 5.

Figure 3:
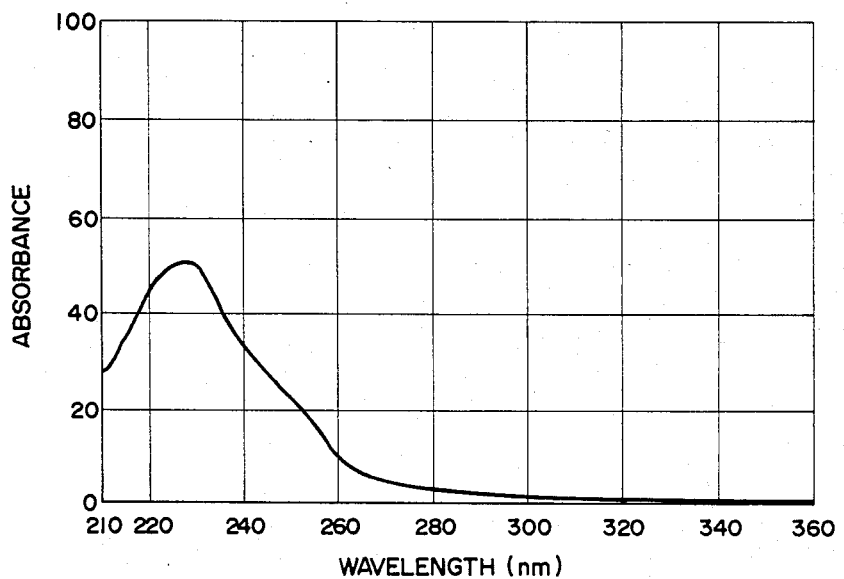
Figure 4:
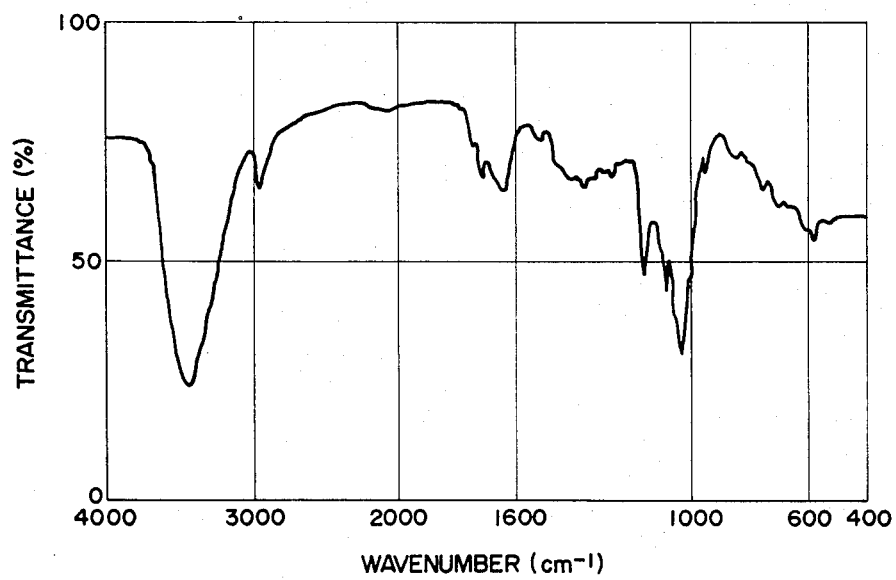
Figure 5:
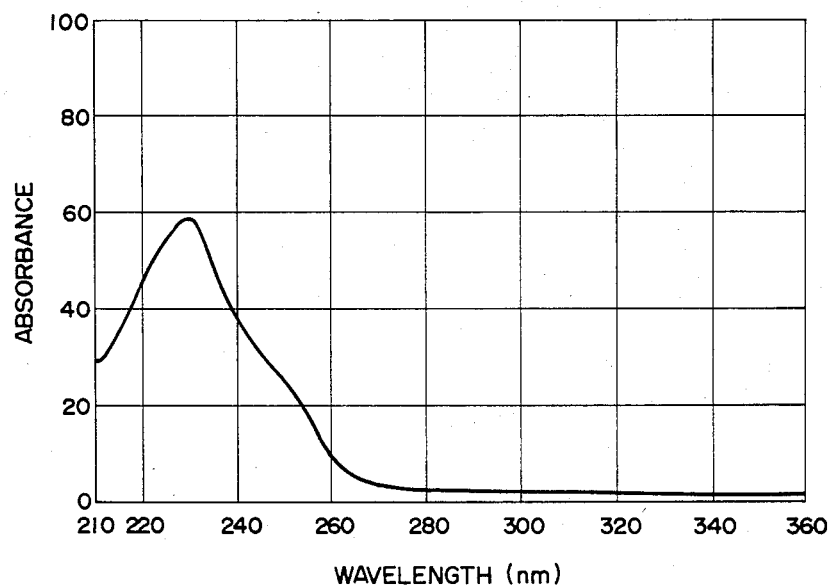
Figure 6:
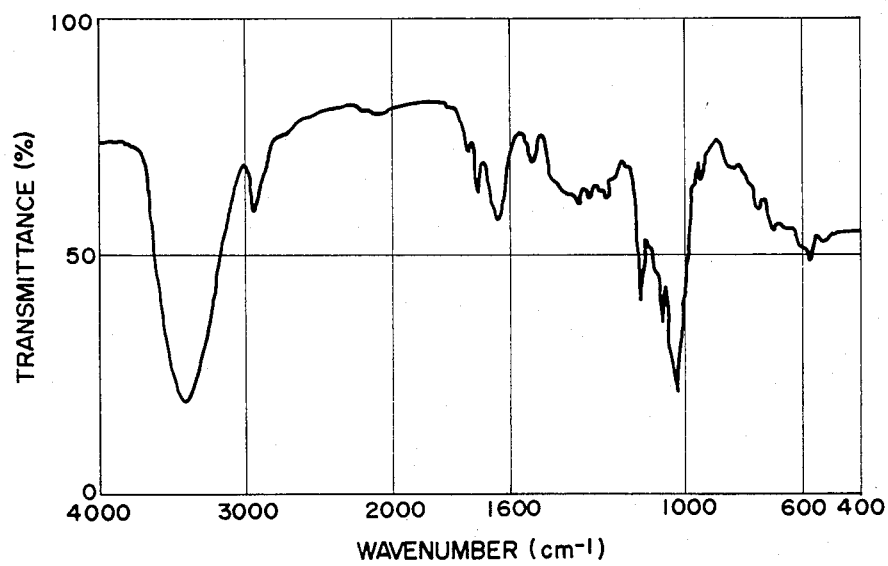

FIG. 3 and FIG. 4 are UV (in water) and IR (KBr), respectively, of the present inclusion compound of lankacidin C prepared in Example 6, and FIG. 5 and FIG. 6 are UV (in water) and IR (KBr), respectively, of the present inclusion compound of lankacidinol prepared in Example 6.

In the case where the inclusion compounds are orally administered, any conventional formation form such as tablets or capsules may be employed without giving any unfavorable influence to their biological activity.

The dosages of the inclusion compound vary depending on diseases, the condition of the subjects and methods of administration. In case of swine dysentery, it is preferable that it is administered in a daily dose of 0.2 to 1.0 g per grown-up swine, once a day or divided into two equal dosages.

The present inclusion compound of lankacidin-group with cyclodextrin is prepared, for example, by dissolving an appropriate amount of cyclodextrin in a solvent, adding a proportional amount of the lankacidin-group to the solution, stirring the mixture, and, if necessary, filtering to remove undissolved materials.

Alternatively, the inclusion compound may be made in solid form such as powders or in crystalline form. The solid form is prepared, for example, by freeze-drying the solution prepared as above or kneading a mixture of the cyclodextrin and the lankacidin-group compound in the molar ratio mentioned below with a small amount of water and freeze-drying the mixture. Water, if necessary, distilled water for injections, is usually used as the solvent. There may be present a small amount as 0.001–1% V/V of alcohols, (e.g., methanol or ethanol) or ketones, (e.g., acetone, methyl ethyl ketone).

The mixture above is usually stirred at a temperature from 0° C. to room temperature until the lankacidin is dissolved, usually for 30 minutes to 24 hours. The freeze-drying is carried out at a temperature of −50° C. to room temperature.

There are four cyclodextrins, α-, β-, γ- and δ-cyclodextrins which are different from each other in polymerization degree. In the present invention, any of these four cyclodextrins can be used, but β-cyclodextrin, γ-cyclodextrin or a mixture thereof is preferable. Cyclodextrin is usually used at a concentration from $10^{-4}$ mole/l to $10^{-1}$ mole/l. The lankacidin-group compound is soluble in water within this range to form inclusion compound with cyclodextrin. $10^{-3}$ mole/l–$10^{-2}$ mole/l and $10^{-3}$ mole/l–$10^{-1}$ mole/l are preferred for β-cyclodextrin and γ-cyclodextrin, respectively.

In the present invention, any of the compounds of the lankacidin-group can be used, but preferably lankacidin A, lankacidin C, lankacidin C 8-esters and lankacidinol. The lankacidin-group compound can be used alone or as a mixture of two or more. Moreover, the lankacidin-group compound may contain a small amount of the other antibiotics or impurities.

The molar ratio of the lankacidin-group compound to cyclodextrin can be calculated, for example, in the following manner:

The lankacidin-group is added to each of solutions containing various amounts of cyclodextrin. The minimum concentration of cyclodextrin which dissolves the maximum amount of the lankacidin-group compound and practical concentrations thereof are determined on the basis of amounts of the lankacidin-group compound dissolved in the cyclodextrin solutions. Then, the molar ratio of cyclodextrin to lankacidin-group compound is calculated by the following equation:

Molar ratio = [Molarity of cyclodextrin]:[(Saturation molarity of lankacidin-group compound in a certain concentration of cyclodextrin-solution) − (saturation molarity of lankacidin-group compound in an aqueous solution)].

The inclusion compound of the present invention is stable in an aqueous solution, although it splits into lankacidin-group moiety and cyclodextrins moiety, when it is in the form of solution or powder, by contacting it with organic solvents (e.g., ethyl acetate, methyl isobutyl ketone) or various carriers (e.g., silica gel, high-porous resins). As shown in Table 1 below, there is almost no difference in antibacterial activity between the inclusion compound and the starting materials thereof. In comparing the antibacterial activity, concentrations of the inclusion compound are calculated in terms of lankacidin-group compound from which the inclusion compound is prepared.

From these data, it is found that a suitable molar ratio of cyclodextrin to lankacidin A is 2:1, when β-cyclodextrin is used, and 1.5:1 when lankacidin C or lankacidinol is used.

TABLE 1

Stability of inclusion compound of lankacidin-group (24° C., for 6 days)

| | | Antibacterial activity against St. aureus 209P*1 (inhibition diameter mm) | | | |
|---|---|---|---|---|---|
| Compound | Solubility | 0 day | 3 days | 6 days | |
| Lankacidin A | Methanol | *2 | 26.75 | 27.0 | 23.25 |
| | β-CD | *3 | 23.75 | 27.0 | 22.0 |
| Lankacidin C | Methanol | *4 | 28.25 | 29.5 | 29.5 |
| | β-CD | *4 | 28.5 | 29.0 | 30.0 |
| Lankacidinol | Methanol | *2 | 25.75 | 27.0 | 30.0 |
| | β-CD | *3 | 28.0 | 28.0 | 30.5 |

*1 Paper disk assay using Trypticase soy agar (Baltimore Biologicals Ltd. U.S.A.) as test culture media.
*2 1000 μg/ml, Lankacidin-group is stable in methanol.
*3 Aqueous solution of the inclusion compound with β-cyclodextrin (1000 μg/ml calculated in terms of lankacidin-group)
*4 100 μg/ml Moreover, a large amount of the present inclusion compound is dissolved in water and it is kept stably therein. Solubility of the inclusion compound in water is greater than that of landacidin-group compounds in water, when the amount of the inclusion compound dissolved is calculated in terms of lankacidin-group compound, and than saturation concentration of cyclodextrin in water so far as cyclodextrin contained in the inclusion compound is concerned (Table 2).

TABLE 2

Solubility of inclusion compound in water

| | solubility (mg/ml) | | | | |
|---|---|---|---|---|---|
| Compound | (1) | (2) | (3)* | (4) | (5) |
| Lankacidin A | 0.181 | 2.69 | 11.3 | >10.0 | >40 |
| Lankacidin C | 0.268 | 3.54 | 11.3 | >10.0 | >37 |
| Lankacidinol | 0.655 | 3.78 | 11.3 | >10.0 | >37 |

(1) Solubility of lankacidin-group in water.
(2) Solubility of lankacidin-group in M/100 β-cyclodextrin solution.
(3) Concentration of β-cyclodextrin of (2).
(4) Solubility (maximum) of the present inclusion compound (calculated in terms of lankacidin-group contained) in water.
(5) Concentration of β-cyclodextrin contained in the inclusion compound of (4).
*The concentration of β-cyclodextrin in its saturated aqueous solution is 18 mg/ml.

Thus, lankacidin-group compound can easily be solubilized and stabilized in water, and it has become possible to administer, for example, in the forms of oral administration or injections. This has enabled development of lankacidin-group as antibacterial agents. One of the biological advantages of the present inclusion compound is an improvement of a bioavailability in a living body. That is, in order to administer lankacidin-group orally or parenterally, it had to be brought into, for example, suspensions by combining with such agents as carboxymethyl cellulose or gum arabic because of poor solubility in water. However, in case of the inclusion compound, it is soluble in water and hence can easily be administered. Moreover, because of enhanced stability in an aqueous solution, it can readily be expected that the rate and amount of absorption into a living body increase. The inclusion compound of the present invention can be administered to the same subjects and for the same purposes as those of the known lankacidin-group mentioned above.

In administering the inclusion compound in the form of an injection, appropriate solubilizing agents commonly used for medicines or veterinary drugs such as alcohol, propylene glycol, and glycerol, pain relievers such as benzyl alcohol or isotonizing agents such as inorganic salts e.g., sodium chloride, sodium hydrogensulfite and other suitable inorganic salts, may be incorporated in the injection.

The present invention will be more precisely illustrated by the following examples. The examples should not be construed to limit the scope of the present invention.

EXAMPLE 1

Powdery lankacidin C was added to an aqueous solution of cyclodextrin (hereinafter referred to as "CD") to have 4 mg/ml of the lankacidin C contained. After the mixture was stirred with a mixer, it was shaken at 5° C. for 2 hours, and passed through filter paper. The absorbancy of the filtrate was measured at 227–229 nm to determine concentration of the lankacidin C.

The results are given in Table 3.

TABLE 3

| | Solubility ($\beta$g/ml) Concentration of CD (Mol/l) | | | | |
|---|---|---|---|---|---|
| CD | 0 | $10^{-4}$ | $10^{-3}$ | $10^{-2}$ | $10^{-1}$ |
| $\beta$-CD | 260 | 280 | 650 | 3730 | — |
| $\gamma$-CD | 260 | 260 | 460 | 2390 | 3790 |

As clearly seen from these data, the lankacidin C shows high solubility in a solution of $\beta$-CD and $\gamma$-CD.

EXAMPLE 2

Solubilities of lankacidin C 8-propionate (hereinafter referred to as "C8-P"), and lankacidin C 14-propionate (hereinafter referred to as "C14-P") in a solution of CD were measured in the same manner as that of Example 1 except that the shaking was continued for one hour.

The results are given in Table 4.

TABLE 4

| Antibiotic | CD | Solubility ($\mu$g/ml) Concentration of CD (Mol/l) | | | | |
|---|---|---|---|---|---|---|
| | | 0 | $10^{-4}$ | $10^{-3}$ | $10^{-2}$ | $10^{-1}$ |
| C8-P | $\beta$-CD | 18 | 46 | 328 | 3840 | — |
| | $\gamma$-CD | | 19 | 54 | 249 | 1610 |
| C14-P | $\beta$-CD | 19 | 21 | 67 | 159 | — |
| | $\gamma$-CD | | 19 | 35 | 114 | 273 |

These data show that, as far as the same concentrations of CD solutions are concerned, the propionate derivatives of the lankacidin Cs dissolve better in a solution of $\beta$-CD than in the other CD solution, and that C8-P has a better solubility than that of C14-P.

EXAMPLE 3

The solubilities of lankacidin A, lankacidin C and lankacidinol in a $\beta$-CD solution were measured in the same manner as that of Example 1 except that the shaking was continued for 16 hours.

The results are given in Table 5.

TABLE 5

| | Solubility ($\mu$g/ml) Concentration of $\beta$-CD (Mol/l) | | | | | | | |
|---|---|---|---|---|---|---|---|---|
| Antibiotic | 0 | $10^{-4}$ | $2 \times 10^{-4}$ | $5 \times 10^{-4}$ | $10^{-3}$ | $2 \times 10^{-3}$ | $5 \times 10^{-3}$ | $10^{-2}$ |
| Lankacidin A | 181 | 195 | 201 | 265 | 400 | 632 | 1370 | 2690 |
| Lankacidin C | 237 | 262 | 304 | 409 | 566 | 934 | 1780 | 3350 |
| Lankacidin C | 268 | | | | 715 | | | 3540 |
| Lankacidinol | 444 | | | | 914 | 1360 | 2130 | 2750 |

It will be seen from these data that the solubilities of lankacidin A, lankacidin C and lankacidinol in $\beta$-CD solution increase in proportion to the concentration of $\beta$-CD starting from the vicinity of $10^{-3}$ Mol/l of $\beta$-CD, and that these lankacidins have the same levels of solubilities despite their difference in the solubility in water containing no $\beta$-CD. This suggests that the tested lankacidins form stable inclusion compounds with $\beta$-CD.

EXAMPLE 4

The solubility of lankacidin-group in a solution of $\beta$-CD ($10^{-2}$ Mol/l) were measured in the same manner as that of Example 1 except that the shaking was continued for 30 minutes to one hour.

The results are given in Table 6.

TABLE 6

| | Solubility ($\mu$g/ml) Concentration of $\beta$-CD (Mol/l) | | |
|---|---|---|---|
| Antibiotic | 0 | $10^{-2}$ | ratio* |
| Lankacidin C 8,14-diacetate | 16.2 | 681 | 42.0 |
| Lankacidin C 14-butylate | 17 | 118 | 6.94 |
| Lankacidin C 8-butylate | 9 | 404 | 44.9 |
| Lankacidin C 8-acetate | 74.3 | 2770 | 37.3 |
| Lankacidinol 2',8,14-triacetate | 36.9 | 332 | 9.0 |
| Lankacidinol 8,14-diacetate | 440 | 1780 | 4.05 |
| Lankacidinol A | 170 | 3070 | 18.1 |
| Iso-lankacidinol | 796 | 3200 | 4.02 |
| Lankacyclinol | 824 | 3610 | 4.38 |

*Solubility in a $10^{-2}$ Mol/l solution of $\beta$-CD/solubility in water.

These data demonstrate that the solubility of lankacidin-group compound is increased owing to cyclodextrin.

EXAMPLE 5

To a solution of $\beta$-cylodextrin (2.04 g) in water (180 ml), was added lankacidin A (450 mg; molar ratio; 2:1). The mixture was stirred at 5° C. for 1.5 hours. After removing a small amount of undissolved materials by filtration, the filtrate was freeze-dried to give 2.4 g of inclusion compound of the lankacidin A as powders.

IR(KBr) cm$^{-1}$: 3400, 2930, 2070, 1730, 1710, 1640, 1510, 1410, 1360, 1330, 1295, 1250, 1150, 1075, 1025, 945, 840, 750, 700, 600, 570, 520.

EXAMPLE 6

To each solution of $\beta$-cyclodextrin (1.7 g) in water (150 ml), was added each of lankacidin C (460 mg) and lankacidinol (460 mg) (molar ratio 1.5:1). The mixture was stirred at 5° C. for 30 minutes, and processed in the same manner as in Example 5 to give an inclusion compound of the lankacidin C (2.1 g) and an inclusion compound of the lankacidinol (2.1 g) as powders.

Table 7 shows $E_{1\,cm}^{1\%}$ of UV-absorption of the tested inclusion compounds.

TABLE 7

| Molar Extinction coefficients at λmax 227–229 nm | |
|---|---|
| Inclusion Compound | $E_{1\ cm}^{1\%}$ |
| Lankacidin A | 150 ± 20 |
| Lankacidin C | 213 ± 20 |
| Lankacidinol | 227 ± 20 |

Lankacidin C inclusion compound
IR(KBr) cm$^{-1}$: 3440, 2940, 2080, 1740, 1710, 1640, 1520, 1415, 1370, 1340, 1300, 1280, 1160, 1080, 1030, 950, 850, 760, 710, 580, 530.

Lankacidinol inclusion compound
IR(KBr) cm$^{-1}$: 3400, 2930, 2060, 1735, 1700, 1640, 1520, 1400, 1370, 1330, 1295, 1270, 1200, 1150, 1080, 1025, 950, 840, 750, 700, 650, 575, 530.

EXAMPLE 7

5 ml each of a methanolic solution containing lankacidin A or C in a concentration of 100 μg per ml was added to 45 ml each of pH 4.5 and pH 7.0 buffer solutions and a buffer solution containing β-cyclodextrin.

Each mixture was placed in a glass vessel, and then sealed. While the mixtures were kept in the vessel at 40° C., 5 ml each was taken out from time to time and extracted with ethyl acetate. The organic layers were dried over anhydrous sodium sulfate and the concentrations of the lankacidin A or C was measured with high-performance liquid chromatography (HPLC).

HPLC Conditions
Apparatus: Water Associates ALC/GPC 240 (Waters Associates Inc., U.S.A.)
Column: μPoracil 30 cm × 3.9 mmφ
Eluent: n-Hexane: isopropyl alcohol: acetic acid (75:25:0.2).

TABLE 8

| Stability of lankacidin A and C in methanolic aqueous solutions | | | | | |
|---|---|---|---|---|---|
| Compound (10 μg/ml) | pH | Amount of β-cyclodextrin added (mg/ml) | Residual rate (%) 0 hr | 4 hr | 6 hr |
| Lankacidin A | 4.5 | none | 100 | 34.5 | |
| | | 10 | 100 | 91.9 | 85.7 |
| | 7.0 | none | 100 | 17.4 | |
| | | 10 | 100 | 58.3 | 48.1 |
| Lankacidin C | 7.0 | none | 100 | | 43.7 |
| | | 10 | 100 | | 88.2 |

As shown in Table 8, β-cyclodextrin increased stabilities of the lankacidin A and C in methanolic aqueous solutions when 1000 times β-CD as much as the lankacidin A or C by weight is added.

EXAMPLE 8

Preparation of an injection swinery

| (1) Lankacidin C | 1.0 g |
|---|---|
| (2) β-cyclodextrin | 3.7 g |
| (3) physiological saline solution | 100 ml |

The same process as that of Example 5 is repeated under sterile conditions to obtain a freeze-dried inclusion compound which is packed in vials in the amount mentioned above and kept under reduced pressure. Required amount of thus prepared inclusion compound is dissolved in said amount of physiological saline solution.

EXAMPLE 9

| Preparation of an injection for swinery | |
|---|---|
| (1) Lankacidin A | 1.0 g |
| (2) β-cyclodextrin | 4.53 g |
| (3) physiological saline solution | 100 ml |

Example 5 is repeated under sterile conditions to obtain a freeze-dried inclusion compound which is packed in vials in the amount mentioned above and kept under reduced pressure. Required amount of thus prepared inclusion compound is dissolved in said amount of physiological saline solution.

Test Example

Efficacy of lankacidin-group inclusion compound with cyclodextrin against swine dysentery.

Test drug: Lankacidin A inclusion compound obtained in Example 5 (titer: 161 mg/g, lankacidin A-β-CD) was used. 10 mg (titer) calculated in terms of lankacidin A is soluble in 1 ml each of physiological saline solution. As a control, lankacidin A itself used in Example 5 was employed.

Test swine: Two pigs which started bloody mucous diarrhea, i.e. typical clinical signs of swine dysentery, were used.

Administration method and amount: Uniform suspension of lankacidin A-β-CD in a sterilized physiological saline solution (titer: 50 mg/ml) was prepared. 5.2 ml (titer: 10 mg/kg) of this suspension was administered to pig No. 1 and 4.9 ml (titer: 7 mg/kg) was administered to pig No. 2 by injecting it into root portion of ear once a day for two days.

For the control (lankacidin A itself), it was tried to prepare an injection with a sterilized physiological saline solution, but suspension could not be obtained due to separation of the drug and furthermore the resultant mixture could not be inhaled into an injector. Thus, administration was impossible.

Estimation of efficacies: Changes of conditions of feces were observed and recorded every day and simultaneously Treponema hyodysenteriae in feces were semi-quantitatively measured on the day when the pigs began to show the sign of dysentery (0th day) and on 1st, 2nd, 3rd, 5th, 7th, and 10th days. That is, fresh excreted feces or feces taken by inserting Cultulette ® (Marion Scientific., U.S.A.) into the anus were coated on the 10% defibrinated sheep blood added Tripticase soy agar (BBL) plate [Jenkinson; Veterinary Record, 384–385, Oct. 24, 1981] containing spectinomycin, colistin and vancomycin in the amounts of 400, 25 and 25 μg/ml, respectively and anaerobical cultivation was effected at 42° C. for 3 days. Degree of hemolysis caused by growth of the bacteria was recorded by five grades of ++++, +++, ++, + and −.

Results: Test results obtained on administration of lankacidin A-β-CD are shown in Table 9. With reference to the conditions of feces, the bloody mucous diarrhea was no longer observed and feces became normal after twice administrations for both the pigs and thus rapid clinical efficacies were recognized for both the pigs. Furthermore, Treponema hyodysenteriae in the feces became negative on the 5th day after administration and were not detected until the 10th day.

Conclusion: Lankacidin A-β-CD exhibited rapid clinical and bacteriological effects when it was intramuscularly administered to pigs infected with swine dysentery.

The control test (on lankacidin A itself) was not effected, because injection was impossible as mentioned hereinbefore.

TABLE 9

Efficacies of lankacidin A-β-cyclodextrin inclusion compounds against swine dysentery by intramuscular administration

| Pig No. | Body weight (kg) | Dose titer: (mg/kg) | Days after starting of administration ||||||||||| 
|---|---|---|---|---|---|---|---|---|---|---|---|---|
| | | | 0 | 1 | 2 | 3 | 4 | 5 | 6 | 7 | 8 | 9 | 10 |
| 1 | 26.0 | 10 | ●▽ (+++ +) | ●▽ (+++ +) | ○ (+++ +) | ○ (+++) | ○ | ○ (−) | ○ | ○ (−) | ○ | ○ | ○ (−) |
| 2 | 35.2 | 7 | ●▽ (+++ +) | ●▽ (+++ +) | ○ (+++ +) | ○ (++) | ○ | ○ (−) | ○ | ○ (−) | ○ | ○ | ○ (−) |

●: indicates bloody mucous diarrhea feces
○: indicates normal feces
▽: indicates administration
( ): indicates rating of degree of excreted bacteria at one of the five classes of "−" to "++++".

We claim:

1. An inclusion compound of a lankacidin-group antibiotic selected from the group consisting of lankacidin A, lankacidin C, lankacidin C 8-ester, lankacidinol and a mixture of said lankacidin-group antibiotics with β- or γ-cyclodextrin.

2. An inclusion compound according to claim 1 wherein the cyclodextrin is β-cyclodextrin.

3. An inclusion compound according to claim 2 wherein the lankacidin-group antibiotic is lankacidin A.

4. A veterinary composition for use in the treatment of swine dysentery which comprises, as an active ingredient, an amount effective for the treatment of swine dysentery of an inclusion compound of a lankacidin-group antibiotic selected from the group consisting of lankacidin A, lankacidin C, lankacidin C 8-ester, lankacidinol and a mixture of said lankacidin-group antibiotics with β- or γ-cyclodextrin and an acceptable carrier therefor.

5. A composition according to claim 4, wherein the composition is in the form of an injectable solution.

6. A method for the treatment of swine dysentery which comprises administering to swine an amount effective for the treatment of swine dysentery of an inclusion compound as defined in claim 1.

* * * * *